United States Patent
Kato et al.

(10) Patent No.: US 11,077,081 B2
(45) Date of Patent: Aug. 3, 2021

(54) AMINO-ACID-CONTAINING COMPOSITION FOR ENHANCING RECOVERY FROM MUSCLE FATIGUE

(71) Applicant: AJINOMOTO CO., INC., Tokyo (JP)

(72) Inventors: Hiroyuki Kato, Kawasaki (JP); Hisamine Kobayashi, Kawasaki (JP); Mayu Sugita, Kawasaki (JP); Hiromi Suzuki, Kawasaki (JP); Masako Mimura, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 245 days.

(21) Appl. No.: 14/175,154

(22) Filed: Feb. 7, 2014

(65) Prior Publication Data

US 2014/0155448 A1    Jun. 5, 2014

Related U.S. Application Data

(63) Continuation of application No. PCT/JP2012/069569, filed on Aug. 1, 2012.

(30) Foreign Application Priority Data

Aug. 8, 2011 (JP) .............................. JP2011-173002

(51) Int. Cl.
| | | |
|---|---|---|
| *A61K 31/197* | (2006.01) | |
| *A61K 31/198* | (2006.01) | |
| *A61K 31/405* | (2006.01) | |
| *A23L 33/175* | (2016.01) | |
| *A61K 31/4172* | (2006.01) | |

(52) U.S. Cl.
CPC .......... *A61K 31/197* (2013.01); *A23L 33/175* (2016.08); *A61K 31/198* (2013.01); *A61K 31/405* (2013.01); *A61K 31/4172* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,716,926 | A * | 2/1998 | Beale | A61K 31/19 426/648 |
| 5,817,329 | A * | 10/1998 | Gardiner | A23L 1/3051 424/439 |
| 6,100,287 | A | 8/2000 | Stevens et al. | |
| 6,224,861 | B1 | 5/2001 | Abe et al. | |
| 2005/0265990 | A1 | 12/2005 | Talbott | |
| 2008/0317886 | A1 | 12/2008 | Sparkman | |
| 2010/0267831 | A1 | 10/2010 | Kobayashi et al. | |

FOREIGN PATENT DOCUMENTS

| | | |
|---|---|---|
| JP | 8-198748 A | 8/1996 |
| JP | 9-52828 A | 2/1997 |
| JP | 9-249556 A | 9/1997 |
| JP | 2000-026290 A | 1/2000 |
| JP | 2005-040117 A | 2/2005 |
| JP | 2006-503105 A | 1/2006 |
| JP | 2006-137706 | 6/2006 |
| JP | 2008-534599 A | 8/2008 |
| JP | 2009-011209 A | 1/2009 |
| JP | 2010-150192 A | 7/2010 |
| WO | WO 99/25331 A1 | 5/1999 |
| WO | WO2004/026294 A1 | 4/2001 |
| WO | WO 2004/112511 A2 | 12/2004 |
| WO | WO 2006/105112 A2 | 10/2006 |
| WO | WO 2006/134752 A1 | 12/2006 |
| WO | WO 2007/056176 A2 | 5/2007 |
| WO | WO 2008/123033 A1 | 10/2008 |

OTHER PUBLICATIONS

Borsheim et al (Am J Physiol Endocrinol Metab 283: E648-E657, 2002).*
Hulmi et al. (Nutrition & Metabolism 2010, 7:51).*
Dan Weinert (JCCA 2009; 53(3):186-194).*
Negro et al (J Sports Med Phys Fitness. Sep. 2008;48(3):347-51).*
Extended Search Report dated Dec. 8, 2014 in European Patent Application No. 12822090.2.
Yoshiharu Shimomura, et al., "Nutraceutical Effects of Branched-Chain Amino Acids on Skeletal Muscle", Journal of Nutrition, vol. 136, No. 2, Feb. 2006, XP002732918, pp. 529S-532S.
Kazunori Nosaka, et al. Effects of amino acid supplementation of muscle so eness and damage, International Journal of sport nutrition & Exercise metabolism, vol. 16, No. 6, Dec. 1, 2006, XP009181300, pp. 620-635.
English translation of the International Search Report and Written Opinion dated Sep. 25 2012 in PCT/JP2012/069569.
Sakoto Watanabe, et al., "Undo ni yoru Chihatsusei Kinnikutsu Oyobi Kinhiro ni Taisuru Bunkisa Amino-san (BCAA) Sesshu no Koka: Undo Mae to Ato no Sesshu" The Japanese Society of Nutrition and Food Science, Taikai oen Yoshishu, vol. 61, Apr. 20, 2001, p. 122.

(Continued)

*Primary Examiner* — Julie Wu
*Assistant Examiner* — John L Van Druff
(74) *Attorney, Agent, or Firm* — Oblon, McClelland, Maier & Neustadt, L.L.P.

(57) ABSTRACT

Administering an amino acid-containing composition, containing the following amino acids (1)-(9), wherein
the molar content ratio of each amino acid to the total content of the amino acids (1)-(9) falls within the following numerical ranges:
(1) leucine 35-66%;
(2) isoleucine 5.0-15%;
(3) valine 5.0-15%;
(4) threonine 7.0-14%;
(5) lysine 8.0-16%;
(6) methionine 2.0-10%;
(7) histidine 0.1-3.5%;
(8) phenylalanine 2.5-8.0%; and
(9) tryptophan 0.1-2.0%,
is effective for enhancing recovery from muscle fatigue.

11 Claims, 5 Drawing Sheets

(56) References Cited

OTHER PUBLICATIONS

Asami Inakuma, et al., "Undo ni yoru Chihatsusei Kinnikutsu Oyobi Kinhirokan ni Taisuru Bunkisa Amino-san (BCAA) Sesshu no Koka" The Japanese Society of Nutrition and Food Science, Sokai Koen Yoshishu, vol. 60, Apr. 1, 2006, p. 101.

Truls Raastad, et al., "Changes in Calpain Activity, Muscle Structure, and Function after Eccentric Exercise" Basic Sciences, Medicine & Science in Sports & Exercise, vol. 42, No. 1, 2010, pp. 86-95.

Robert S. Thiebaud, Exercise-Induced Muscle Damage: Is it detrimental or beneficial?, Journal of Trainology 2012, vol. 1, pp. 36-44).

McKune et al., Acute Exercise-Induced Muscle Injury, Biology of Sport, vol. 29, No. 1, 2012, pp. 3-10.

* cited by examiner

AMINO-ACID-CONTAINING COMPOSITION FOR ENHANCING RECOVERY FROM MUSCLE FATIGUE

CROSS REFERENCES TO RELATED APPLICATIONS

This application is a continuation of International Patent Application No. PCT/JP2012/069569, filed on Aug. 1, 2012, and claims priority to and Japanese Patent Application No. 2011-173002, filed on Aug. 8, 2011, both of which are incorporated herein by reference in their entireties.

BACKGROUND OF THE INVENTION

Field of the Invention

The present invention relates to amino acid-containing compositions for enhancing recovery from muscle fatigue and to methods of enhancing recovery from muscle fatigue.

Discussion of the Background

It is known that many factors are involved in muscle fatigue. Examples of the factors include: (1) accumulation of metabolic by-products such as $H^+$, inorganic phosphate (Pi), ammonia, and the like; (2) fever; (3) impaired reabsorption of $Ca^{2+}$; (4) depolarization of ion gradient of $K^+$ and $Na^+$; (5) shortage of ATP for muscle contraction; (6) depletion of energy substances such as muscle glycogen, liver glycogen, and the like; and (7) damage of muscle and the like. Particularly, damage of muscle caused by an excessive exercise load (hereinafter to be also referred to as muscle damage) leads to muscular pain and decreased muscle strength, and has been reported to be one of the important factors causing impaired performance of athletes and the like (see Medicine & Science in sports and exercise, 42(1), pp. 86-95, 2010, which is incorporated herein by reference in its entirety). Therefore, an early recovery from such muscle damage is a particularly major problem for, for example, sports players referred to as so-called top athletes who are constantly requested to show high performance, and the like.

In the meantime, it has been reported that a particular amino acid-containing composition can prevent or improve sarcopenia in elderly citizens (decrease in the amount of skeletal muscle along with aging), and can impart or enhance kokumi to/of protein drinks such as milk and the like (see JP-A-2008-534599 and JP-A-2009-11209, which are incorporated herein by reference in their entireties). However, an action to enhance recovery from muscle damage caused by an excessive exercise load and the like has not been reported at all.

Thus, there remains a need for compositions for and methods of enhancing recovery from muscle fatigue.

SUMMARY OF THE INVENTION

Accordingly, it is one object of the present invention to provide novel amino acid-containing compositions for enhancing recovery from muscle fatigue.

It is another object of the present invention to provide novel methods for enhancing recovery from muscle fatigue These and other objects, which will become apparent during the following detailed description, have been achieved by the inventors' discovery that in the muscle damage induced by an excessive exercise load, myofibrillar protein, cytoskeletal protein bound to myofibril and sarcolemma, extracellular matrix and the like are damaged. These damaged proteins are removed by proteolysis and thereafter new proteins are synthesized, whereby recovery from the muscle damage occurs. The present inventors have conducted intensive studies and surprisingly found that ingestion of a composition containing particular amino acids increases the synthesis rate of damaged protein, accelerates recovery from muscle damage, and enhances recovery from muscle fatigue through recovery from the muscle damage. Based on such findings, they have conducted further studies and completed the present invention.

Accordingly, the present invention provides the following:

(1) An amino acid-containing composition for enhancing recovery from muscle fatigue, comprising the following amino acids (1)-(9), wherein
the molar content ratios of the respective amino acids to the total content of said amino acids (1)-(9) fall within the following numerical ranges:
(1) leucine 35-66%
(2) isoleucine 5.0-15%
(3) valine 5.0-15%
(4) threonine 7.0-14%
(5) lysine 8.0-16%
(6) methionine 2.0-10%
(7) histidine 0.1-3.5%
(8) phenylalanine 2.5-8.0%
(9) tryptophan 0.1-2.0%.

(2) The amino acid-containing composition of the abovementioned (1), wherein the muscle fatigue is muscle fatigue caused by muscle damage.

(3) The amino acid-containing composition of the abovementioned (2), wherein the muscle damage is muscle damage after exercise.

(4) The amino acid-containing composition of the abovementioned (3), wherein the muscle damage after exercise is muscle damage after eccentric contraction exercise.

(5) The amino acid-containing composition of the abovementioned (1), wherein the enhanced recovery from muscle fatigue is prophylaxis and/or improvement of muscular pain.

(6) The amino acid-containing composition of the abovementioned (1), wherein the enhanced recovery from muscle fatigue is prophylaxis and/or improvement of muscle weakness.

(7) The amino acid-containing composition of the abovementioned (1), wherein the enhanced recovery from muscle fatigue is prophylaxis and/or improvement of muscle damage.

(8) A method of enhancing recovery from muscle fatigue, comprising administering an effective amount of an amino acid-containing composition comprising the following amino acids (1)-(9), wherein
the molar content ratios of the respective amino acids to the total content of said amino acids (1)-(9) fall within the following numerical ranges:
(1) leucine 35-66%
(2) isoleucine 5.0-15%
(3) valine 5.0-15%
(4) threonine 7.0-14%
(5) lysine 8.0-16%
(6) methionine 2.0-10%
(7) histidine 0.1-3.5%
(8) phenylalanine 2.5-8.0%
(9) tryptophan 0.1-2.0%.

(9) Use of an amino acid-containing composition comprising the following amino acids (1)-(9), wherein
the molar content ratios of the respective amino acids to the total content of said amino acids (1)-(9) fall within the following numerical ranges:

(1) leucine 35-66%
(2) isoleucine 5.0-15%
(3) valine 5.0-15%
(4) threonine 7.0-14%
(5) lysine 8.0-16%
(6) methionine 2.0-10%
(7) histidine 0.1-3.5%
(8) phenylalanine 2.5-8.0%
(9) tryptophan 0.1-2.0% for producing an enhancer of recovery from muscle fatigue.

According to the present invention, an amino acid-containing composition for enhancing recovery from muscle fatigue can be provided.

Taking the amino acid-containing composition of the present invention can promote synthesis of myofibrillar protein, cytoskeletal protein bound to myofibril and sarcolemma, and extracellular matrix, which were damaged by an excessive exercise load, and can enhance recovery from the muscle damage.

In addition, taking the amino acid-containing composition of the present invention can prevent and/or improve muscular pain and muscle weakness.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The amino acid-containing composition of the present invention contains (1) leucine, (2) isoleucine, (3) valine, (4) threonine, (5) lysine, (6) methionine, (7) histidine, (8) phenylalanine and (9) tryptophan as essential components.

In the amino acid-containing composition of the present invention, the molar content ratios of the respective amino acids to the total content of the amino acids (1)-(9) are generally (1) leucine 35-66%, (2) isoleucine 5.0-15%, (3) valine 5.0-15%, (4) threonine 7.0-14%, (5) lysine 8.0-16%, (6) methionine 2.0-10%, (7) histidine 0.1-3.5%, (8) phenylalanine 2.5-8.0%, and (9) tryptophan 0.1-2.0%, preferably (1) leucine 35-57%, (2) isoleucine 5.0-15%, (3) valine 5.0-15%, (4) threonine 7.0-14%, (5) lysine 8.0-16%, (6) methionine 2.0-10%, (7) histidine 0.1-3.5%, (8) phenylalanine 2.5-8.0%, and (9) tryptophan 0.1-2.0%, more preferably (1) leucine 35-50%, (2) isoleucine 5.0-15%, (3) valine 5.0-15%, (4) threonine 7.0-14%, (5) lysine 8.0-16%, (6) methionine 2.0-10%, (7) histidine 0.1-3.5%, (8) phenylalanine 2.5-8.0%, and (9) tryptophan 0.1-2.0%. When contents of the amino acids are within the above-mentioned ranges, an effect of enhancing recovery from muscle fatigue is markedly exhibited.

The amino acid-containing composition of the present invention may further contain other components in addition to the aforementioned amino acids (1)-(9). Examples of other components include amino acids such as serine, glutamine, arginine, and the like; carbohydrate; lipid; vitamin; mineral; and the like, with preference given to amino acids such as serine, glutamine, arginine, and the like.

The amino acids (1)-(9) and amino acids that may be contained as other components each may be any of L-form, D-form and DL-form, preferably L-form or DL-form, more preferably L-form.

The amino acids (1)-(9) and amino acids that may be contained as other components each may be not only in a free form but also in the form of a salt. The salt form is not particularly limited as long as it is a salt of the amino acid (1)-(9) or amino acid that may be contained as other component, and is acceptable as a medicament or food. For example, an acid addition salt, a salt with a base and the like can be mentioned.

Examples of the acid that forms a salt of the amino acids (1)-(9) or amino acid that may be contained as other component, and is acceptable as a medicament or food include inorganic acids such as hydrochloric acid, hydrogen bromide, sulfuric acid, phosphoric acid, and the like; organic acids such as acetic acid, lactic acid, citric acid, tartaric acid, maleic acid, fumaric acid, monomethyl sulfuric acid, and the like; and the like.

Examples of the base that forms a salt of the amino acids (1)-(9) or amino acid that may be contained as other component, and is acceptable as a medicament or food include inorganic bases such as sodium, potassium, calcium, ammonia, and the like; organic bases such as ethylenediamine, propylenediamine, ethanolamine, monoalkylethanolamine, dialkylethanolamine, diethanolamine, triethanolamine, and the like; and the like.

The salt of the amino acids (1)-(9) or amino acid that may be contained as other component may be a hydrate (hydrate salt). As such hydrate, 1-6 hydrates and the like can be mentioned.

The amino acids (1)-(9) and amino acids that may be contained as other components may be extracted and purified from animals, plants, and the like containing them, or obtained by chemical synthesis method, fermentation method, or gene recombination method.

The amino acid-containing composition of the present invention can be, for example, formulated by adding a pharmaceutically acceptable pharmaceutical carrier and the like, and provided as a pharmaceutical product. Moreover, for example, it can be provided as food or drink (including food for specified health uses, food with health claims such as food with nutrient function claims and the like, nutrition aid food, other health foods, supplement) by adding materials for food or drink, food additive, and the like.

When the amino acid-containing composition of the present invention is provided as a pharmaceutical product, the product may be for oral administration or parenteral administration. Specific examples of the dosage form include solid preparations such as a powder, fine granule, granule, tablet (including sugar-coated tablet, film-coated tablet), capsule, pill, divided powder, powder, gel, gum, cream, and the like;

liquid preparations such as an injection (for intramuscular injection, intravenous injection), tubal liquid, elixir, suspension, syrup, emulsion, ampoule etc., and the like.

Examples of the pharmaceutically acceptable pharmaceutical carrier include celluloses such as crystalline cellulose, hydroxypropylcellulose and the like and derivatives thereof; excipients such as natural polymer compounds (e.g., gum arabic, sodium alginate, and the like) and the like; binders such as guar gum, stearic acid, high molecular weight polyvinylpyrrolidone, and the like; lubricants such as talc, polyethylene glycol 6000 and the like; disintegrants such as adipic acid and the like; surfactants such as sucrose fatty acid ester, soybean lecithin, polyoxyethylene hydrogenated castor oil, polyoxyethylene monostearate, and the like; thickeners such as sodium carboxymethylcellulose, carboxy vinyl polymer, xanthan gum, gelatin, and the like; coating agents such as ethyl acrylate/methyl methacrylate copolymer dispersion, caramel, Carnauba wax, shellac, pullulan, and the like; pH adjusters such as citric acid, sodium citrate, acetic acid, sodium acetate, sodium hydroxide, and the like; antioxidants such as erythorbic acid, butylhydroxyanisole, propyl gallate, and the like; flavoring agents such as aspartame, licorice extract, saccharin, and the like; preservatives such as sodium benzoate, sodium edetate, sorbic acid, sodium sorbate, methyl p-hydroxybenzoate, butyl p-hydroxybenzoate, and the like; colorants such as ferric oxide red, yellow iron oxide, black iron oxide, carmine, Food Color blue No. 1, Food Color Yellow No. 4, Food Color Red No. 2, and the like; and the like.

When the amino acid-containing composition of the present invention is provided as a food or drink, it can be produced as, for example, liquid products such as drink and the like, emulsion products such as yogurt and the like, jelly products such as jelly and the like, jelly drink, gum product, powder product, granular product, sheet product, capsule product, tablet product, solid product such as snack bar, cookie and the like, and the like.

Examples of the material for foods and drinks or food additive include a sweetener, colorant, preservative, thickening stabilizer, antioxidant, color coupler, bleach, fungicide, gum base, bittering agent, enzyme, brightener, acidulant, seasoning, emulsifier, toughening agent, manufacturing agent, flavor, spice, and the like.

The amino acid-containing composition of the present invention can be produced by formulation techniques and food production techniques known per se.

The daily ingestion amount of the amino acid-containing composition of the present invention is individually determined based on the level of muscle fatigue, age, sex, body weight, diet condition and the like. It is generally 3 to 22 g, preferably 6 to 20 g. The aforementioned amount is preferably ingested in 1 to 3 portions per day.

The ingestion period is also individually determined based on the level of muscle fatigue, age, sex, body weight, diet condition and the like. It is generally 1 day to 2 weeks, preferably 5 days to 1 week.

Since the amino acid-containing composition of the present invention has an action of promoting synthesis of myofibrillar protein, cytoskeletal protein bound to myofibril and sarcolemma, and extracellular matrix, which were damaged by an excessive exercise load, it is useful as a pharmaceutical product, food or drink for enhancing recovery from the muscle damage.

In the present specification, the term "muscle fatigue" refers to a condition wherein a transient pathological symptom (e.g., muscular pain, perceived fatigue of muscle, muscle stiffness, muscle lameness etc.) and/or hypoactivity (e.g., muscle weakness etc.) are/is developed due to a load applied onto the muscle. Therefore, recovery from the pathological symptom (e.g., recovery from muscular pain, recovery from perceived fatigue of muscle etc.) and/or recovery from hypoactivity (e.g., recovery from muscle weakness etc.) mean(s) recovery from muscle fatigue. The recovery from muscle fatigue, for example, can be accomplished by the recovery of the amount of desmin protein that decreased in the muscle cell, recovery of the amount of the collagen protein which is the main component of extracellular matrix and the like. As the muscle fatigue, muscle fatigue caused by muscle damage and the like can be mentioned.

Since the amino acid-containing composition of the present invention has an action of promoting synthesis of myofibrillar protein, cytoskeletal protein bound to myofibril and sarcolemma, and extracellular matrix, which were damaged by an excessive exercise load, it is useful as a pharmaceutical product, food or drink for the prophylaxis and/or improvement of the muscle damage. Therefore, the amino acid-containing composition of the present invention is particularly useful as a pharmaceutical product, food or drink for enhancing recovery from muscle fatigue caused by muscle damage.

In the present specification, the term "muscle damage" includes muscle damage (small damage on the connective tissue surrounding myofibril or muscle fiber) caused by an excessive exercise load and the like, as well as secondary damage (e.g., infiltration of inflammatory cells such as neutrophil and the like, tissue denaturation due to enzyme reaction and the like) caused by inflammatory reaction associated with said damage and the like.

The development of muscle damage can be judged using the amount of desmin protein, which is one kind of cytoskeletal protein bound to myofibril or sarcolemma, in the muscle as an index. The measurement method of the amount of desmin protein in the muscle is as described below.

That is, the muscle is homogenized, protein is fractionated by SDS-PAGE, and the fraction is transferred to a transfer membrane and quantified by Westernblot using a desmin antibody.

The muscle damage specifically refers to the condition wherein the amount of desmin protein in the muscle is lower than that during resting.

Muscle damage occurs, for example, after exercise such as eccentric contraction exercise and the like. Here, the term eccentric contraction exercise refers to an exercise by which the muscle exerts force while the muscle is stretched.

Since the amino acid-containing composition of the present invention enhances recovery from the muscle fatigue, it is also useful as a pharmaceutical product, food or drink for the prophylaxis and/or improvement of muscle pain.

Since the amino acid-containing composition of the present invention enhances recovery from the muscle fatigue, it is also useful as a pharmaceutical product, food or drink for the prophylaxis and/or improvement of muscle weakness.

Other features of the invention will become apparent in the course of the following descriptions of exemplary embodiments which are given for illustration of the invention and are not intended to be limiting thereof.

EXAMPLES

Production of Amino Acid-Containing Composition.
1. Amino Acid-Containing Composition A Various amino acids in predetermined amounts were weighed and mixed to give amino acid-containing composition A having the composition shown in Table 1.

TABLE 1

| starting material name | molar composition ratio (%) to (1)-(9) |
|---|---|
| (1) L-leucine | 42.1 |
| (2) L-isoleucine | 11.2 |
| (3) L-valine | 13.0 |
| (4) L-threonine | 10.8 |
| (5) L-lysine hydrochloride | 12.6 |
| (6) L-methionine | 3.1 |
| (7) L-histidine hydrochloride 1-hydrate | 1.1 |
| (8) L-phenylalanine | 5.6 |
| (9) L-tryptophan | 0.5 |

Figure 1:
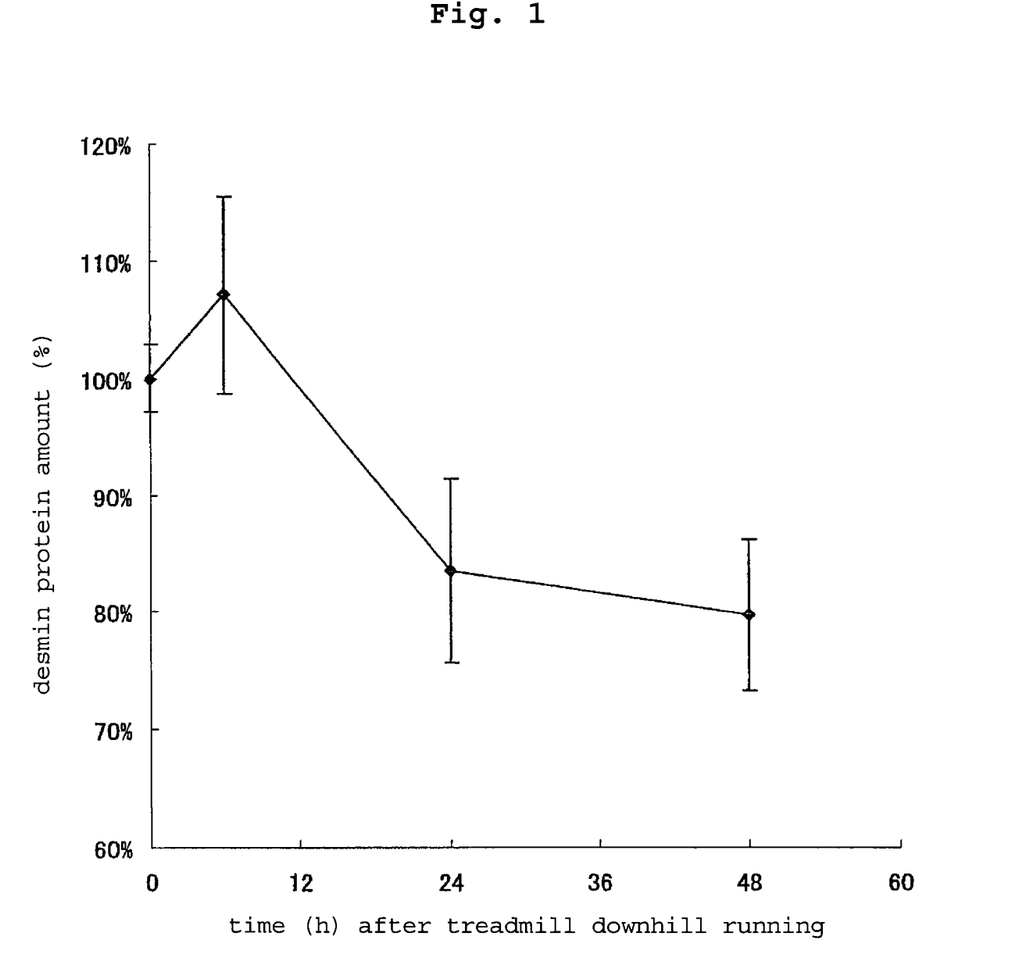
FIG. 1 is a graph showing the time-course changes in the desmin protein amount in the muscle of the muscle damage model rat produced in Reference Example 1.

Reference Example 1. Time-Course Changes of Desmin Protein Amount in Muscle Due to Treadmill Downhill Running 8-week-old female Wistar rats were used for treadmill downhill running to produce a muscle damage model rat. The treadmill downhill running included running at an inclination angle of −13.5° for 5 minutes at a rate of 17 m/minute, followed by resting for 2 minutes. With this exercise as 1 set, 26 sets were performed. The time-course changes in the desmin protein amount in the muscle of the muscle damage model rat are shown in FIG. 1.

Experimental Example 1. Evaluation of Prophylactic and/or Improvement Effect on Muscular Pain Using 10-week-old male SD rats, a 1 g/kg dose of amino acid-containing composition A or water was orally administered, and an eccentric contraction load was applied 30 minutes after the oral administration to induce muscle damage.

Figure 2:
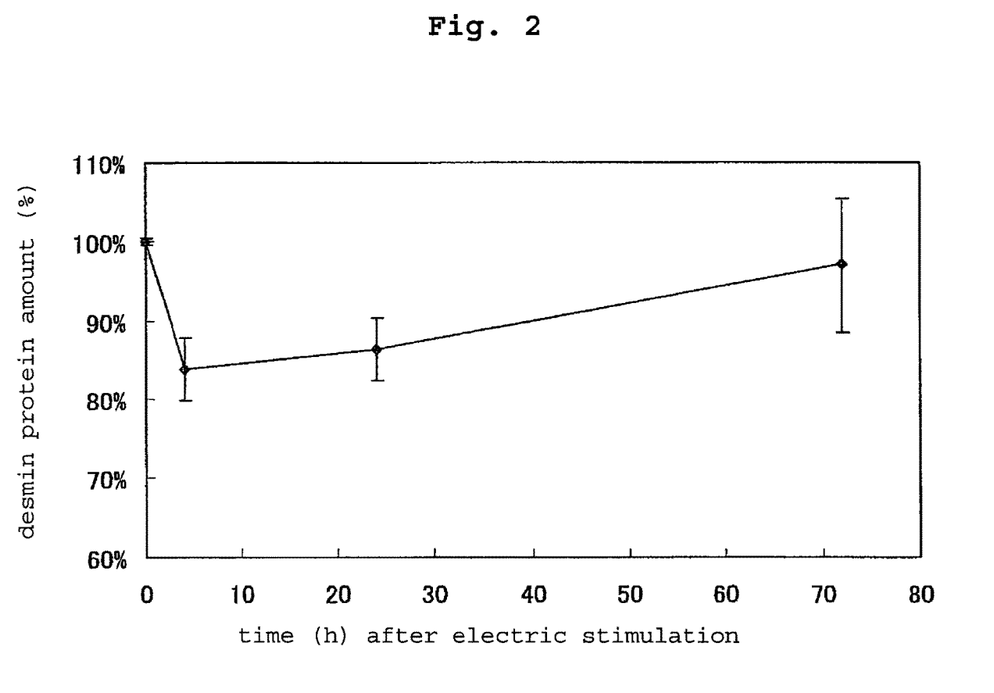
FIG. 2 is a graph showing the time-course changes in the desmin protein amount in the muscle of the rat due to the eccentric contraction load in Experimental Example 1.

The eccentric contraction load included, under pentobarbital anesthesia, inserting a cathode near the common peroneal nerve of the rat and an anode near the sciatic nerve of the rat, contracting the muscle for 1 second by applying an electric stimulation at 50 Hz at a current value of 3 times the twitch threshold, while simultaneously stretching paws by a motor to the opposite direction of the muscle contraction, and resting the rat thereafter for 3 seconds. With this exercise as 1 set, it was repeated for 500 sets. The time-course changes in the desmin protein amount in the muscle of the rat due to the eccentric contraction load for the water group are shown in FIG. 2.

After 2 hours from the eccentric contraction load, a 1 g/kg dose of amino acid-containing composition A or water was orally administered again, after which muscular pain was evaluated.

Figure 3:
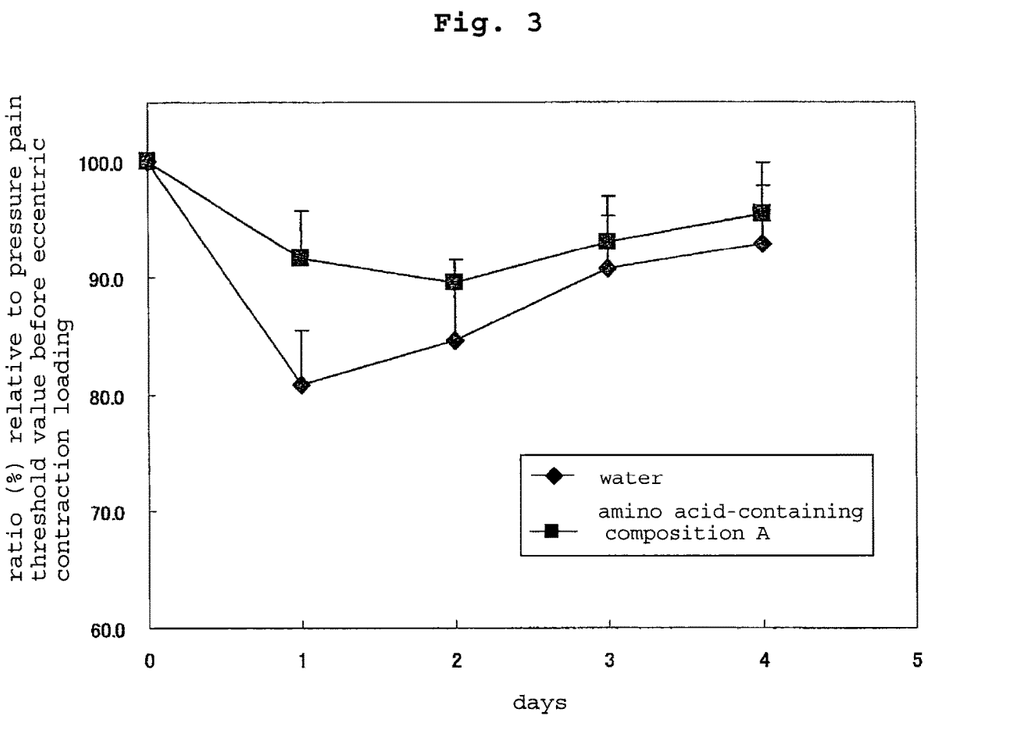
FIG. 3 is a graph showing the time-course changes in the pressure pain threshold measured in Experimental Example 1.

Muscular pain was evaluated by observing the time-course changes of the threshold value of muscle pressure pain. The pressure pain threshold value was determined by placing a cone-type probe (diameter 2.6 mm) of Randall-Selitto analgesia meter on tibialis anterior muscle of a conscious rat, increasing a transdermal load at a rate of 157 mN/s, and measuring the load at the moment the rat draws the paw upon feeling the pain. When the muscular pain occurs, the pressure pain threshold value decreases. The results are shown in FIG. 3. In FIG. 3, the pressure pain threshold value is shown in a ratio (%) relative to the pressure pain threshold value before the eccentric contraction loading as 100%.

As is clear from the results shown in FIG. 3, muscle damage was developed by the eccentric contraction load, and the pressure pain threshold value decreased (that is, onset of muscular pain). However, administration of amino acid-containing composition A suppressed the decrease in the pressure pain threshold value. Therefore, administration of amino acid-containing composition A was confirmed to improve muscular pain.

Experimental Example 2. Influence of Amino Acid-Containing Composition on Synthesis Rates of Desmin Protein and Muscle Collagen Protein 8-Week-old female Wistar rats were used for treadmill downhill running to produce a muscle damage model rat. The treadmill downhill running included running at an inclination angle of −13.5° for 5 minutes at a rate of 17 m/minute, followed by resting for 2 minutes. With this exercise as 1 set, 26 sets were performed.

Immediately after the completion of the treadmill downhill running, a 1 g/kg dose of amino acid-containing composition A or water was orally administered, and the syntheses rates of the desmin protein and muscle collagen protein in 30 minutes from 20 to 50 minutes after the oral administration were measured by a flooding dose technique using stable isotope-labeled proline. The synthesis rate of the desmin protein is shown in FIG. 4, and the synthesis rate of the muscle collagen protein is shown in FIG. 5.

Figure 4:
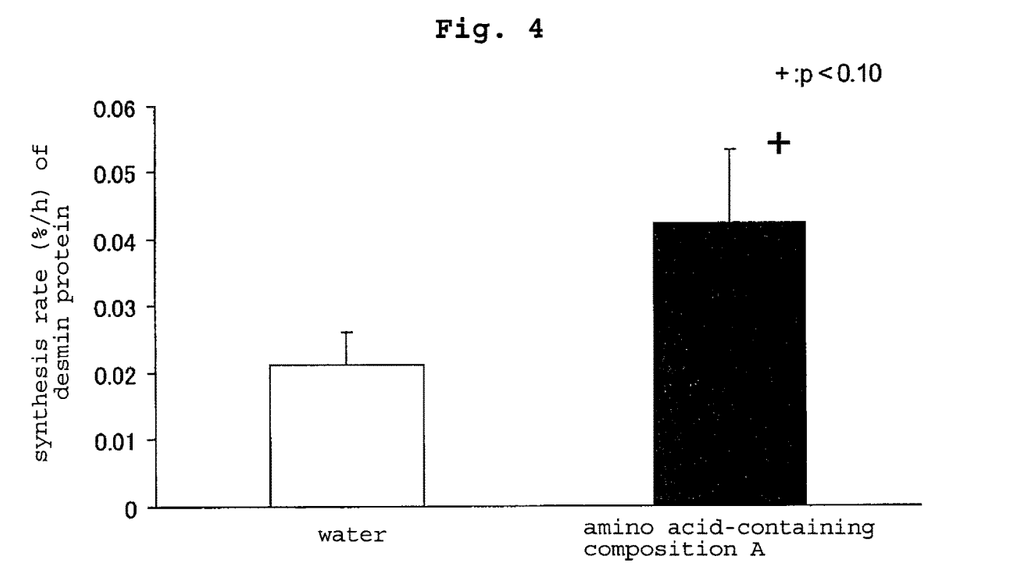
FIG. 4 is a graph showing the synthesis rate of desmin protein measured in Experimental Example 2.
Figure 5:
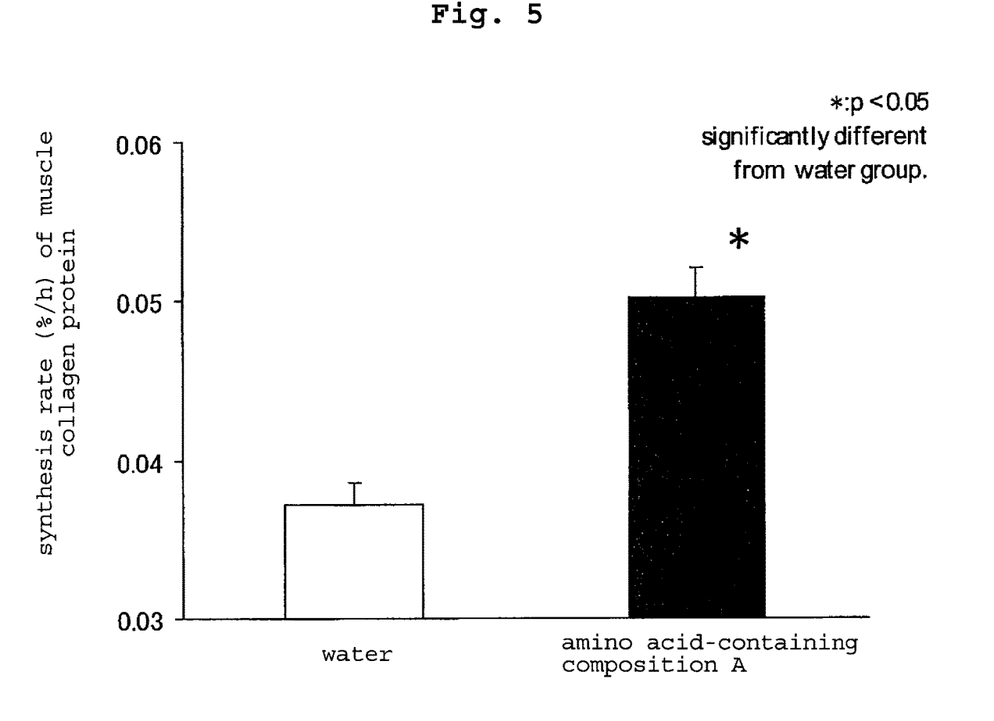
FIG. 5 is a graph showing the synthesis rate of muscle collagen protein measured in Experimental Example 2.

As is clear from the results shown in FIGS. 4 and 5, administration of amino acid-containing composition A promoted syntheses of the desmin protein and muscle collagen protein. Therefore, administration of amino acid-containing composition A was confirmed to lead to the enhanced recovery of muscle damage.

Experimental Example 3. Evaluation of Muscle Damage Recovery Effect

Using 11-week-old male SD rats, a 1 g/kg dose of amino acid-containing composition A or water was orally administered, and an eccentric contraction load was applied 30 minutes after the oral administration to induce muscle damage.

The eccentric contraction load included, under isoflurane anesthesia, adhering a cathode near the tibialis anterior muscle and head of fibula of the rat and an anode near the distal end of tibialis anterior muscle of the rat, contracting the muscle for 1 second by applying an electric stimulation at 50 Hz at a current value of 4 mA, while simultaneously stretching paws by a motor to the opposite direction of the muscle contraction, and resting the rat thereafter for 3 seconds. With this exercise as 1 set, it was repeated for 500 sets.

After 1 hour from the eccentric contraction load, a 1 g/kg dose of amino acid-containing composition A or water was orally administered again, and after 24 hours from the oral administration, muscle was collected.

Figure 6:
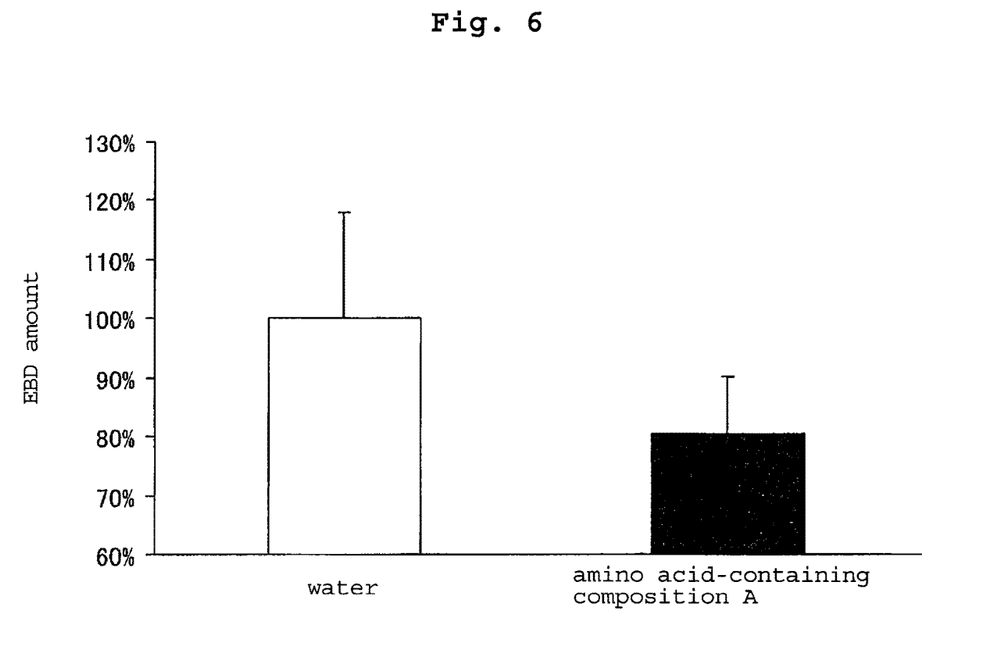
FIG. 6 is a graph showing the EBD amount measured in Experimental Example 3.

The muscle damage was evaluated by intraperitoneally administering 0.5% evansblue dye (hereinafter to be abbreviated as "EBD") to the rat at a dose of 10 ml/kg immediately before the eccentric contraction load, thereafter dissolving the muscle collected from the rat, applied with the eccentric contraction load, in KOH, and measuring the amount of intramuscular EBD. Since a larger amount of EBD is incorporated into the muscle when the muscle damage is more severe, the level of muscle damage can be evaluated by measuring the amount of EBD incorporated into the muscle. The amount of EBD in the muscle collected from the rat applied with the eccentric contraction load is shown in FIG. 6. The amount of EBD in FIG. 6 is shown in a ratio (%) relative to the water administration group as 100%.

As is clear from the results shown in FIG. 6, administration of amino acid-containing composition A decreased the amount of the EBD incorporated into the muscle. Therefore, administration of amino acid-containing composition A was confirmed to enhance recovery of muscle damage caused by an eccentric contraction load.

Experimental Example 4. Evaluation of Effect of Enhancing Recovery of Muscle Strength Using 11- to 12-week-old male SD rats, a 1 g/kg dose of amino acid-containing composition A or water was orally administered, and an eccentric contraction load was applied 30 minutes after the oral administration to induce muscle damage.

The eccentric contraction load included, under isoflurane anesthesia, adhering a cathode near the tibialis anterior muscle and head of fibula of the rat and an anode near the distal end of tibialis anterior muscle of the rat, contracting the muscle for 1 second by applying an electric stimulation at 50 Hz at a current value of 4 mA, while simultaneously stretching paws by a motor to the opposite direction of the muscle contraction, and resting the rat thereafter for 3 seconds. With this exercise as 1 set, it was repeated for 500 sets.

After 1 hour from the eccentric contraction load, a 1 g/kg dose of amino acid-containing composition A or water was orally administered again, after which muscle strength was measured after 6 hours from the eccentric contraction load.

Figure 7:
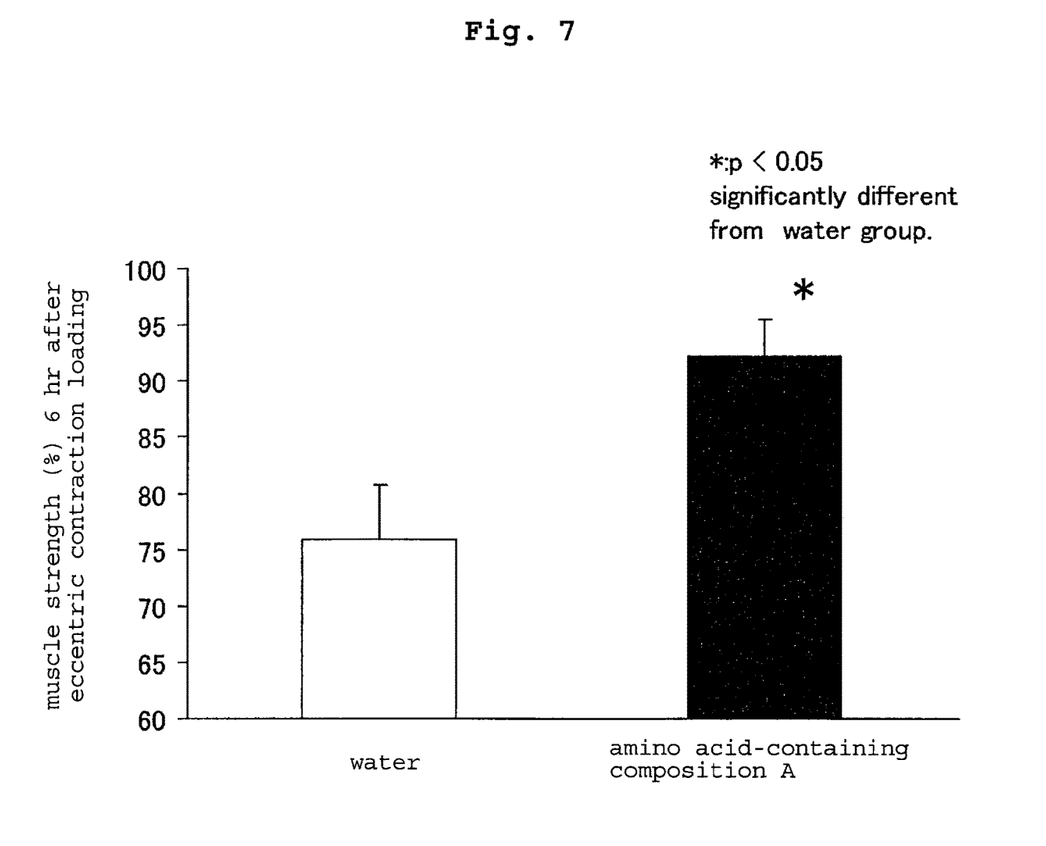
FIG. 7 is a graph showing the muscle strength 6 hours after the eccentric contraction load measured in Experimental Example 4.

The muscle strength was measured by mounting a tension meter on a paw of the rat under anesthesia, adhering electrodes in the same manner as in the above-mentioned eccentric contraction load, applying an electric stimulation at 50 Hz at a current value of 4 mA, and measuring the isometric strength with paw dorsiflexion. The muscle strength 6 hours after the eccentric contraction load is shown in FIG. 7. In FIG. 7, the value of muscle strength is shown in a ratio (%) relative to that before the eccentric contraction load as 100%.

As is clear from the results shown in FIG. 7, the eccentric contraction load remarkably decreases the muscle strength, but administration of amino acid-containing composition A was confirmed to enhance recovery of the muscle strength lowered by an eccentric contraction load.

INDUSTRIAL APPLICABILITY

According to the present invention, an amino acid-containing composition for enhancing recovery from muscle fatigue can be provided.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of enhancing recovery from muscle weakness caused by muscle damage due to eccentric contraction exercise, comprising: administering to a subject in need thereof an effective amount of an amino acid-containing composition, wherein the amino acid-containing composition comprises, in a molar content ratio with respect to a total amount of leucine, isoleucine, valine, threonine, lysine, methionine, histidine, phenylalanine, and tryptophan,
    (1) 35 to 66% of leucine,
    (2) 5.0 to 15% of isoleucine,
    (3) 5.0 to 15% of valine,
    (4) 7.0 to 14% of threonine,
    (5) 8.0 to 16% of lysine,
    (6) 2.0 to 10% of methionine,
    (7) 0.1 to 3.5% of histidine,
    (8) 2.5 to 8.0% of phenylalanine, and
    (9) 0.1 to 2.0% of tryptophan,
    wherein the amino acid-containing composition is administered to the subject after the exercise.

2. The method of claim 1, wherein the amino acid-containing composition comprises 42 to 66% of leucine, 0.1 to 1.1% of histidine, and 2.5 to 5.6% of phenylalanine in the molar content ratio with respect to the total amount of leucine, isoleucine, valine, threonine, lysine, methionine, histidine, phenylalanine, and tryptophan.

3. The method of claim 1, wherein the amino acid-containing composition comprises, in the molar content ratio with respect to the total amount of leucine, isoleucine, valine, threonine, lysine, methionine, histidine, phenylalanine, and tryptophan,
    (1) about 42% of leucine,
    (2) about 11% of isoleucine,
    (3) about 13% of valine,
    (4) about 11% of threonine,
    (5) about 13% of lysine,
    (6) about 3% of methionine,
    (7) about 1% of histidine,
    (8) about 6% of phenylalanine, and
    (9) about 1% of tryptophan.

4. A method of enhancing recovery of an amount of collagen protein in muscle decreased due to eccentric contraction exercise, comprising: administering to a subject in need thereof an effective amount of an amino acid-containing composition such that recovery of an amount of collagen protein in muscle is enhanced, wherein the amino acid-containing composition comprises, in a molar content ratio with respect to a total amount of leucine, isoleucine, valine, threonine, lysine, methionine, histidine, phenylalanine, and tryptophan,
    (1) 35 to 66% of leucine,
    (2) 5.0 to 15% of isoleucine,
    (3) 5.0 to 15% of valine,
    (4) 7.0 to 14% of threonine,
    (5) 8.0 to 16% of lysine,
    (6) 2.0 to 10% of methionine,
    (7) 0.1 to 3.5% of histidine, (8) 2.5 to 8.0% of phenylalanine, and
(9) 0.1 to 2.0% of tryptophan,
wherein the amino acid-containing composition is administered to the subject after the exercise.

5. The method of claim 4, wherein the amino acid-containing composition comprises, in the molar content ratio with respect to the total amount of leucine, isoleucine, valine, threonine, lysine, methionine, histidine, phenylalanine, and tryptophan,
   (1) about 42% of leucine,
   (2) about 11% of isoleucine,
   (3) about 13% of valine,
   (4) about 11% of threonine,
   (5) about 13% of lysine,
   (6) about 3% of methionine,
   (7) about 1% of histidine,
   (8) about 6% of phenylalanine, and
   (9) about 1% of tryptophan.

6. A method of enhancing recovery of an amount of desmin protein in muscle decreased due to eccentric contraction exercise, comprising: administering to a subject in need thereof an effective amount of an amino acid-containing composition such that recovery of an amount of desmin protein in muscle is enhanced, wherein the amino acid-containing composition comprises, in a molar content ratio with respect to a total amount of leucine, isoleucine, valine, threonine, lysine, methionine, histidine, phenylalanine, and tryptophan,
   (1) 35 to 66% of leucine,
   (2) 5.0 to 15% of isoleucine,
   (3) 5.0 to 15% of valine,
   (4) 7.0 to 14% of threonine,
   (5) 8.0 to 16% of lysine,
   (6) 2.0 to 10% of methionine,
   (7) 0.1 to 3.5% of histidine,
   (8) 2.5 to 8.0% of phenylalanine, and
   (9) 0.1 to 2.0% of tryptophan,
wherein the amino acid-containing composition is administered to the subject after the exercise.

7. The method of claim 6, wherein the amino acid-containing composition comprises, in the molar content ratio with respect to the total amount of leucine, isoleucine, valine, threonine, lysine, methionine, histidine, phenylalanine, and tryptophan,
   (1) about 42% of leucine,
   (2) about 11% of isoleucine,
   (3) about 13% of valine,
   (4) about 11% of threonine,
   (5) about 13% of lysine,
   (6) about 3% of methionine,
   (7) about 1% of histidine,
   (8) about 6% of phenylalanine, and
   (9) about 1% of tryptophan.

8. The method of claim 1, wherein an amount of the amino acid-containing composition administered to the subject is from 3 to 22 g.

9. The method of claim 4, wherein the amount of collagen protein is decreased due to exercise as compared to an amount of collagen protein in muscle in the subject prior to the exercise.

10. The method of claim 6, wherein the amount of desmin protein is decreased due to exercise as compared to an amount of desmin protein in muscle in the subject.

11. The method of claim 1, wherein an amount of the amino acid-containing composition administered to the subject is from 6 to 20 g.

* * * * *

UNITED STATES PATENT AND TRADEMARK OFFICE
CERTIFICATE OF CORRECTION

PATENT NO. : 11,077,081 B2
APPLICATION NO. : 14/175154
DATED : August 3, 2021
INVENTOR(S) : Kato et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 301 days.

Signed and Sealed this
Sixth Day of December, 2022

Katherine Kelly Vidal
*Director of the United States Patent and Trademark Office*